(12) United States Patent
Tabatadze

(10) Patent No.: US 10,738,005 B2
(45) Date of Patent: *Aug. 11, 2020

(54) AZIRIDINYL CONTAINING COMPOUNDS AND METHODS OF INACTIVATING NUCLEIC ACID MOLECULES USING THE SAME

(71) Applicant: ZATA Pharmaceuticals, Inc, Worcester, MA (US)

(72) Inventor: David R. Tabatadze, Worcester, MA (US)

(73) Assignee: ZATA Pharmaceuticals, Inc., Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/213,052

(22) Filed: Dec. 7, 2018

(65) Prior Publication Data

US 2019/0106386 A1    Apr. 11, 2019

Related U.S. Application Data

(63) Continuation of application No. 15/036,675, filed as application No. PCT/US2014/065367 on Nov. 13, 2014, now Pat. No. 10,173,976.

(60) Provisional application No. 61/903,480, filed on Nov. 13, 2013.

(51) Int. Cl.
   *C07D 203/12*  (2006.01)
   *A61L 2/16*    (2006.01)

(52) U.S. Cl.
   CPC .............. *C07D 203/12* (2013.01); *A61L 2/16* (2013.01)

(58) Field of Classification Search
   CPC ................................ A61L 2/16; C07D 203/12
   USPC ......................................................... 514/183
   See application file for complete search history.

(56) References Cited

U.S. PATENT DOCUMENTS

| | | |
|---|---|---|
| 4,605,698 A | 8/1986 | Briden |
| 5,612,320 A | 3/1997 | Wurtman et al. |
| 5,612,329 A | 3/1997 | Callery et al. |
| 7,208,528 B1 * | 4/2007 | Vermeulin ............ A61K 31/16 514/311 |
| 10,173,976 B2 * | 1/2019 | Tabatadze ................ A61L 2/16 |
| 2004/0092583 A1 * | 5/2004 | Shanahan-Prendergast ............... A61K 31/00 514/469 |
| 2005/0074743 A1 | 4/2005 | Purmal et al. |
| 2007/0161006 A1 * | 7/2007 | Wu ...................... C12Q 1/6883 435/6.14 |
| 2008/0187932 A1 * | 8/2008 | Wu ...................... C12Q 1/6883 435/6.14 |

FOREIGN PATENT DOCUMENTS

CN       101392108 A      3/2009

OTHER PUBLICATIONS

Aoki, K. R, et al., "Mode of Action of Botulinum Neurotoxins: Current Vaccination Strategies and Molecular Immune Recognition", Critical Reviews™ in Immunology (2010); vol. 30:2: pp. 167-187.
Bovier, P. A., "Epaxal®: a Virosomal Vaccine to Prevent Hepatitis A Infection", Expert Rev. Vaccines (2008); vol. 7:8; pp. 1141-1150.
Griffin, D. E., et al., "Measles Vaccines", Frontiers in Bioscience (2008), vol. 13; pp. 1352-1370.
Thierry-Carstensen, B. et al., "Experience with Monocomponent Acellular Pertussis Combination Vaccines for Infants, Children, Adolescents and Adults —a Review of Safety, Immunogenicity, Efficacy and Effectiveness Studies and 15 years of Field Experience"; Vaccine (2013); vol. 31; pp. 5178-5191.
Verma, R. et al., Whole-Cell Inactivated Leptospirosis Vaccine: Future Prospects. Human Vaccine & Immunotherapeutics (2013); vol. 94: pp. 763-765.
The International Search Report and Written Opinion for PCT/US14/65367, dated Jan. 28, 2015; 9 pages.

* cited by examiner

*Primary Examiner* — Sabiha N Qazi
(74) *Attorney, Agent, or Firm* — Fox Rothschild LLP

(57) ABSTRACT

Described herein are compositions and compounds having one or more aziridinyl groups, and methods of making the same. The compounds can also have one or more nitrogen atoms that each can be positively charged. The composition and compounds can inactivate one or more nucleic acid molecules (e.g. a DNA and/or a RNA from a pathogen) in a sample. The sample can comprise a blood or blood product (e.g., donated blood). The compositions and compounds can inactivate any nucleic acid present in a blood or blood product, thereby making the blood or blood product safe for use (e.g., in a transfusion).

27 Claims, 8 Drawing Sheets

G: N⁷, N¹, NH₂ bonded to C², N³

C: NH₂ bonded to C¹, N³

A: N⁷, NH₂ bonded to C², N¹, N³

T: N³          U: N³

4A

4B

4C

4D

FIGS. 6A-6B
6A
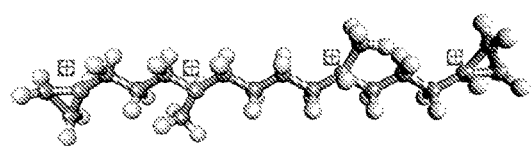 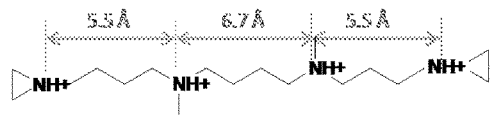
6B
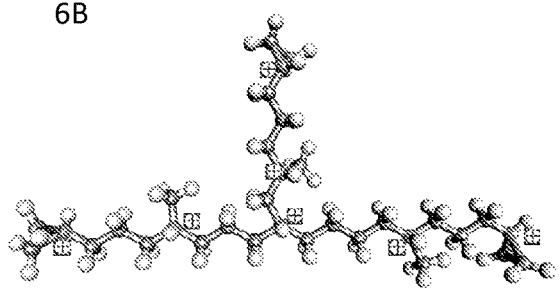 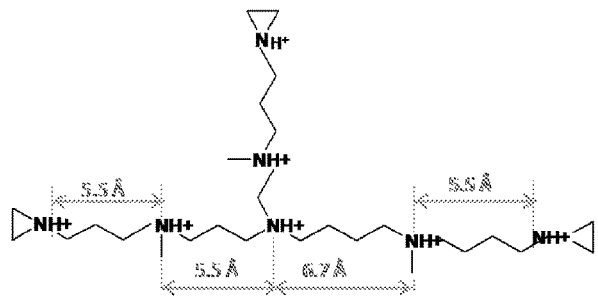

AZIRIDINYL CONTAINING COMPOUNDS AND METHODS OF INACTIVATING NUCLEIC ACID MOLECULES USING THE SAME

CROSS-REFERENCE TO RELATED APPLICATIONS

This application is a continuation of U.S. application Ser. No. 15/036,675, filed May 13, 2016, which is a 371 of International Patent Application No.: PCT/US2014/065367, filed Nov. 13, 2014, which claims the benefit of priority to U.S. Application No. 61/903,480, filed Nov. 13, 2013, each of which is incorporated herein by reference in its entirety.

BACKGROUND

Identification and removal of pathogenic material from biological samples is time-consuming and expensive. Further, not all pathogenic material can be easily identified and targeted. For example, donated blood (e.g., for blood transfusions) requires pathogen inactivation or removal in blood and blood products intended for transfusion. Under current safety procedures for collecting blood, many blood donors are rejected due to potentially contaminated blood. Once blood is collected, it is subject to multiple blood tests. These tests are expensive, time-consuming, and require specialized facilities and personnel to complete. Unfortunately, these tests do not eliminate all risk of the transmission of infectious diseases in a blood transfusion. For instance, many pathogens are simply not tested or a test may not exist for emerging pathogens. Even those pathogens that are tested for may not be detected during an incubation or "window" period.

Though screening procedures are available, there is still a risk of transmission of infectious diseases via blood transfusion. In order to maintain the integrity, purity and adequacy of the blood supply, new donor screening assays and donor deferral schemes have been constantly implemented. These schemes, however, help generate blood supply shortages and make safe blood products costly.

Several molecules have been tested as anti-pathogen devices (APDs) (also referred to herein as "anti-pathogen compounds" or "APCs") targeting pathogen genetic material.

For instance, synthetic oligonucleotides have been widely tested as APCs in blood product. These compounds were never further developed due to poor cell penetration and their nonspecific therapeutic effect. Several molecules, such as methylene blue, amotosalen HCl, S-303 frangible anchor linker effector (FRALE), and riboflavin were investigated as potential candidate agents for pathogen genome knockdown in red blood cells. These compounds can damage the genomes of blood borne pathogens (BBP) through photomodification, but none had sufficient efficacy due to the competitive light absorption by naturally occurring chromophores present in blood. Another compound, aziridinyl ethylamine, enabled inactivation of a wide range of blood borne pathogens. However, the concentration and incubation time necessary for inactivation of blood borne pathogens was excessive and aziridinyl ethylamine provoked undesirable side effects. Anthracene-polyamine conjugates and a large number of aminoindole analogs were tested against malaria, but were also ineffective.

Formaldehyde and β-propiolactone are commonly used for vaccine production (e.g. dead or inactivated vaccines). However, these compounds possess undesirable side effects that lower vaccine efficacy. For example, formaldehyde and β-propiolactone alkylate nucleophilic centers of antigenic epitopes of pathogens, affecting the quality of vaccines.

Gamma irradiation is used for the sterilization of cosmetic and medical compositions (e.g., lotions, creams, gels, transfusion fluids, others). However, gamma rays can change the physical and chemical properties of these compositions. To avoid such adverse effects, small chemical molecules such as ethylene oxide, formaldehyde, and β-propiolactone are widely used. However, they easily vaporize, are highly chemical active and are associated with health related effects.

Accordingly, there is a need for compositions, compounds and systems to inactivate pathologic contamination in a variety of sources in the medical and cosmetic industries.

SUMMARY

The present disclosure relates generally to compositions and compounds having one or more aziridinyl groups. The compositions and compounds described herein can be used for inactivating nucleic acid molecules. Specifically disclosed are compounds and methods for inactivating one or more nucleic acid molecules (e.g., DNA or RNA) in a sample.

In one embodiment, the invention relates to a compound having structure (I):

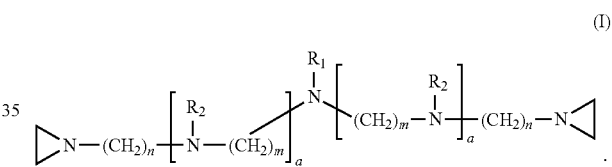

(I)

In the compound having structure (I), $R_1$ is selected from the group consisting of H, $CH_3$, $CH_2CH_3$, $CH(CH_3)_2$, an alkyl, OH, F, and structure (II):

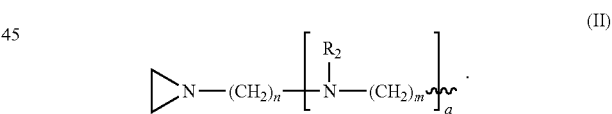

(II)

$R_2$ is, independently for each occurrence, selected from the group consisting of H, $CH_3$, and

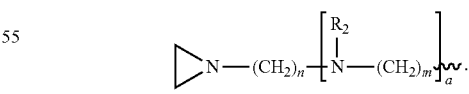

a is, independently for each occurrence, 0, 1, 2 or 3, and m and n are, independently for each occurrence, 1, 2, 3, 4 or 5.

In some embodiments, the compound having structure (I) comprises a pharmaceutically acceptable salt, hydrate, or solvate thereof In one embodiment, the compound has structure (I), wherein $R_1$ is structure (II):

[structure: ▷N—(CH₂)ₙ—[N(R₂)—(CH₂)ₘ]ₐ—], wherein each $R_2$ is $CH_3$, each a is 1, each m is 4, and each n is 3.

In another embodiment, the compound has structure (I), wherein $R_1$ is $CH_3$ or $CH_2CH_3$, and wherein each $R_2$ is $CH_3$, each a is 1, each m is 4, and each n is 3.

In another embodiment, the compound has structure (I), wherein $R_1$ is $CH_3$, wherein a first a is 0 and a second a is 1; $R_2$ is $CH_3$; m is 4; and each n is 3.

In another embodiment, the invention relates to a compound having structure (III):

$$R_3\text{—}N(R_1)\text{—}R_2 \quad (III)$$

wherein $R_1$ is selected from the group consisting of H, $CH_3$, $CH_2CH_3$, $CH(CH_3)_2$, an alkyl, OH, F, and

[structure: ▷N—(CH₂)ₙ—[N(R₄)—(CH₂)ₘ]ₐ—].

$R_2$ is

[structure: ▷N—(CH₂)ₙ—[N(R₄)—(CH₂)ₘ]ₐ—]  or

[structure: ▷N—(CH₂)ₙ—[N—CH(R₉)—CH(R₈)—CH(R₇)—CH(R₆)(R₅)]_b—].

$R_3$ is

[structure: ▷N—(CH₂)ₙ—[N—CH(R₉)—CH(R₈)—CH(R₇)—CH(R₆)(R₅)]_b—].

$R_4$ is, independently for each occurrence, selected from the group consisting of H, $CH_3$, and

[structure: ▷N—(CH₂)ₙ—[N(R₄)—(CH₂)ₘ]ₐ—].

$R_5$, $R_6$, and $R_9$ are, independently for each occurrence, selected from the group consisting of H, $CH_3$ or an alkyl; $R_7$ is, independently for each occurrence, selected from the group consisting of H, $CH_3$, $CH_2CH_3$, an alkyl, $NO_2$, OH, $CH_2OH$, and $(CH_2)_2OH$; $R_8$ is, independently for each occurrence, selected from the group consisting of H, $CH_3$, $CH_2CH_3$, an alkyl, and

[structure: ▷N—(CH₂)ₙ—[N(R₄)—(CH₂)ₘ]ₐ—].

a and b are, independently for each occurrence, 0, 1, 2 or 3. m and n are, independently for each occurrence, 1, 2, 3, 4, or 5.

In some embodiments, the compound having structure (III) comprises a pharmaceutically acceptable salt, hydrate, or solvate thereof.

In one embodiment of the compound having structure (III), $R_1$ is $CH_3$. In another embodiment of the compound having structure (III), $R_2$ is

[structure: ▷N—(CH₂)ₙ—[N(R₄)—(CH₂)ₘ]ₐ—]

and a is 0 and n is 3.

In some embodiments, the compounds (e.g., having structure (I) or (III)) described herein comprise one or more nitrogen atoms that are positively charged. In some embodiments, each nitrogen atom in the compounds described herein is positively charged. In one embodiment, one or more nitrogen atoms are positively charged at a pH of about 6 to about 8. In one embodiment, one or more nitrogen atoms are positively charged at a pH of about 6.5 to about 7.5. In one embodiment, one or more nitrogen atoms are positively charged at a pH of about 7.35 to about 7.45. In one embodiment, each nitrogen atom is positively charged at a pH of about 6 to about 8. In one embodiment, each nitrogen atom is positively charged at a pH of about 6.5 to about 7.5. In one embodiment, each nitrogen atom is positively charged at a pH of about 7.35 to about 7.45.

Another embodiment of the invention relates to a method of inactivating one or more nucleic acids in a sample comprising administering a (one or more) compound having structure (I) and/or structure (III). In one embodiment, the method comprises administering a composition comprising a compound having structure (I) and/or structure (III) to the sample.

In one embodiment, the method comprises administering a compound having structure (I) to the sample.

(I)

[structure: ▷N—(CH₂)ₙ—[N(R₂)—(CH₂)ₘ]ₐ—N(R₁)—[(CH₂)ₘ—N(R₂)]ₐ—(CH₂)ₙ—N◁]

In the compound having structure (I), $R_1$ is selected from the group consisting of H, $CH_3$, $CH_2CH_3$, $CH(CH_3)_2$, an alkyl, OH, F, and

[structure: ▷N—(CH₂)ₙ—[N(R₂)—(CH₂)ₘ]ₐ—].

$R_2$ is, independently for each occurrence, selected from the group consisting of H, $CH_3$, and

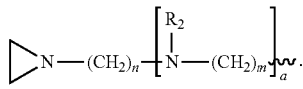

a is, independently for each occurrence, 0, 1, 2 or 3. m and n are, independently for each occurrence, 1, 2, 3, 4 or 5.

In some embodiments, the method comprises administering a compound having structure (I) comprising a pharmaceutically acceptable salt, hydrate, or solvate thereof.

In one embodiment, the invention relates to a method of inactivating one or more nucleic acids in a sample comprising administering a composition comprising one or more compounds having structure (I), structure (III), or a combination thereof to a sample, wherein the sample comprises one or more nucleic acids to be inactivated.

In one embodiment, the method of inactivating one or more nucleic acids in a sample comprises administering one or more compounds having structure (I), structure (III), or a combination thereof, whereby the compound inactivates each nucleic acid by alkylating the nucleic acid.

In some embodiments, each of the one or more nucleic acids to be inactivated comprises a DNA and/or a RNA. In some embodiments, one of the nucleic acids comprises a pathogen nucleic acid sequence. In another embodiment, the pathogen nucleic acid sequence is a viral and/or bacterial nucleic acid sequence.

In another embodiment of the methods described herein, the sample comprises a blood and/or a blood product. In some embodiments, a buffy coat has been removed from the blood or blood product.

In some embodiments, the sample comprises a cosmetic composition. In another embodiment, the sample comprises a medical composition. In another embodiment, the sample is used for a vaccine or vaccine production.

Further understanding of the invention can be obtained by reference to the following detailed description in conjunction with the associated drawings, which are described briefly below.

BRIEF DESCRIPTION OF DRAWINGS

FIGS. 6A-6B illustrates the spacing of the positive charges in two embodiments of the compound disclosed herein.

DETAILED DESCRIPTION

Figures 1A, 1B:
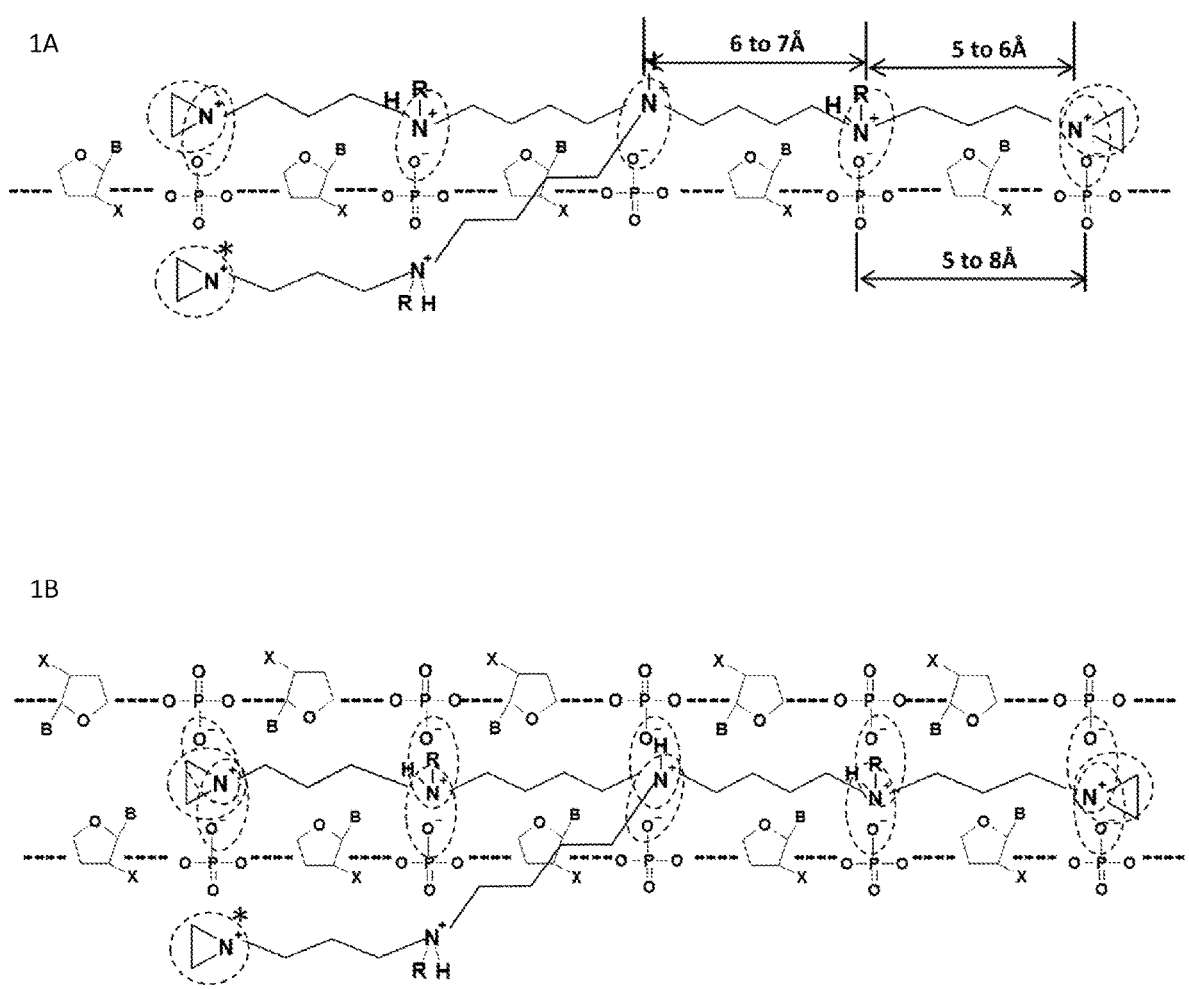
FIGS. 1A-1B illustrates aggregation of one embodiment of the compound with single stranded nucleic acid (FIG. 1A) and double stranded nucleic acid (FIG. 1B).

The invention described herein relates to compositions and compounds having one or more aziridinyl groups. These compounds have one or more nitrogen atoms that can each be positively charged. These compositions and compounds can inactivate one or more nucleic acid molecules (e.g. from a pathogen) in a sample. The compounds provided herein can also enable preservation of all antigenic epitopes. The compounds can selectively aggregate with one or more nucleic acids, thereby promoting their inactivation.

The nucleic acids to be inactivated can be alkylated at one or more sites by the compositions and compounds. The methods provided herein comprise preservation of one or more antigenic determinants for vaccine production.

The compositions and compounds of the present invention can have a high affinity toward nucleic acid molecules. For example, the compounds described herein can bind to nucleic acid molecules at low concentrations (e.g., μM, nM, or pM). These compounds can also have a molecular weight (MW) of less than about 1000 g/mol. The compounds can penetrate through cell membranes, cell walls, or capsids of organisms and pathogens. The compounds described herein also have molecular structures that promote hybridization with one or more nucleic acid molecules through simultaneous ion-pairing (SIP). The compounds further comprise chemically active moieties that can inactivate nucleic acid molecules. The compounds are chemically stable and reactive under ambient conditions.

In one embodiment, the invention relates to a composition comprising a compound having structure (I):

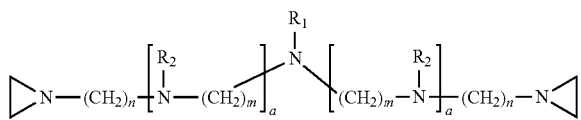

(I)

In the compound having structure (I), $R_1$ is selected from the group consisting of H, $CH_3$, $CH_2CH_3$, $CH(CH_3)_2$, an alkyl, OH, F, and structure (II):

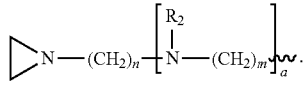

(II)

$R_2$ is, independently for each occurrence, selected from the group consisting of H, $CH_3$, and

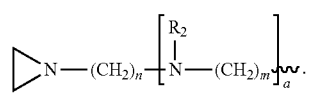

a is, independently for each occurrence, 0, 1, 2 or 3, and m and n are, independently for each occurrence, 1, 2, 3, 4 or 5.

In some embodiments, the compound having structure (I) comprises a pharmaceutically acceptable salt, hydrate, or solvate thereof In one embodiment, the compound has structure (I), wherein $R_1$ is structure (II):

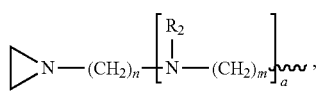

and wherein each $R_2$ is $CH_3$, each a is 1, each m is 4, and each n is 3.

In another embodiment, the compound has structure (I), wherein $R_1$ is $CH_3$ or $CH_2CH_3$, and wherein each $R_2$ is $CH_3$, each a is 1, each m is 4, and each n is 3.

In another embodiment, the compound has structure (I), wherein $R_1$ is $CH_3$, wherein a first a is 0 and a second a is 1; $R_2$ is $CH_3$; m is 4; and each n is 3.

In another embodiment, the invention relates to a composition comprising and/or a compound having structure (III):

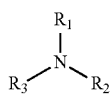

(III)

wherein $R_1$ is selected from the group consisting of H, $CH_3$, $CH_2CH_3$, $CH(CH_3)_2$, an alkyl, OH, F, and

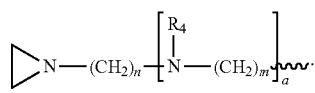

$R_2$ is

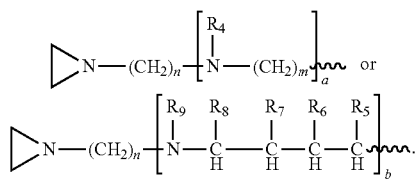

$R_3$ is

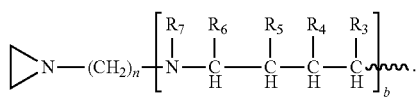

$R_4$ is, independently for each occurrence, selected from the group consisting of H, $CH_3$, and

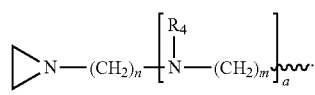

$R_5$, $R_6$, and $R_9$ are, independently for each occurrence, selected from the group consisting of H, $CH_3$ or an alkyl; $R_7$ is, independently for each occurrence, selected from the group consisting of H, $CH_3$, $CH_2CH_3$, an alkyl, $NO_2$, OH, $CH_2OH$, and $(CH_2)_2OH$; $R_8$ is, independently for each occurrence, selected from the group consisting of H, $CH_3$, $CH_2CH_3$, an alkyl, and

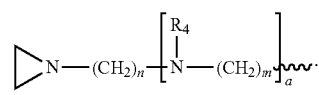

a and b are, independently for each occurrence, 0, 1, 2 or 3. m and n are independently for each occurrence, 1, 2, 3, 4, or 5.

In some embodiments, the compound having structure (III) comprises a pharmaceutically acceptable salt, hydrate, or solvate thereof.

In one embodiment of the compound, $R_1$ is $CH_3$. In another embodiment, $R_2$ is

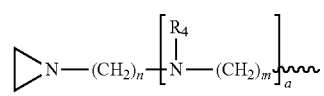

and a is 0 and n is 3.

In some embodiments, the compound having structure (I) comprises a pharmaceutically acceptable salt, hydrate, or solvate thereof In some embodiments, a composition comprises a (one or more) compound having structure (I) and a (one or more) compound having structure (III). In some embodiments, a composition comprises at least one compound having structure (I), at least one compound having structure (III), or a combination thereof. In some embodiments, the composition comprises one or more, two or more, three or more, four or more, five or more, six or more, seven or more eight or more, nine or more, or ten or more compounds having structure (I) and/or (III). As used herein, "compound" or "compounds" is any compound having the general structure (I) or (III), unless specifically stated otherwise.

In another embodiment, the present invention relates to compositions and compounds having one or more aziridinyl groups. In some embodiments, the methylene carbons in the heterocycle (aziridinyl group) are bonded to hydrogen atoms. In other embodiments, one or more of the hydrogens are substituted (e.g., replaced) with another functional group (e.g., $CH_3$, $CH_2CH_3$). Each aziridinyl group, shown herein in structures (I) and (III), can have the general structure (IV):

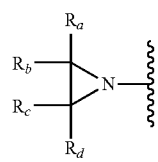

(IV)

For example, $R_a$, $R_b$, $R_c$, and $R_d$ are, each independently, H, $CH_3$, $CH_2CH_3$, a straight chained alkyl, or a branched alkyl.

In some embodiments, the compounds (e.g., having structure (I) and/or (III)) described herein comprise one or more nitrogen atoms. The one or more nitrogen atoms can be positively charged. In some embodiments, each nitrogen atom in the compounds described herein is positively charged. In one embodiment, one or more nitrogen atoms are positively charged at a pH of about 6 to about 8. In one embodiment, one or more nitrogen atoms are positively charged at a pH of about 6.5 to about 7.5. In one embodiment, the compound (e.g., having structure (I) and/or (III)) has one or more nitrogen atoms are positively charged at a pH of about 7.35 to about 7.45. In one embodiment, each nitrogen atom is positively charged at a pH of about 6 to about 8. In one embodiment, each nitrogen atom is positively charged at a pH of about 6.5 to about 7.5. In another embodiment, each nitrogen atom is positively charged at a pH of about 7.35 to about 7.45.

In some embodiments, the compound having structure (I) and/or (III), has 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more nitrogen atoms. In one embodiment, the compound (e.g., having structure (I) and/or (III)) has 4 nitrogen atoms. In one embodiment, the compound has 5 nitrogen atoms. In one embodiment, the compound has 6 nitrogen atoms. In one embodiment, the compound has 7 nitrogen atoms. In one embodiment, the compound has 8 nitrogen atoms. In one embodiment, the compound has 9 nitrogen atoms. In one embodiment, the compound has 10 nitrogen atoms.

In another embodiment, at least one positive charge (e.g., on a nitrogen atom) in the compounds described herein, e.g., having structure (I) or (III), can form an ion pair. For example, in the presence of a polynucleotide (e.g., a nucleic acid molecule), a compound having structure (I) or (III) can form one or more ion pairs with the negative charges on the polynucleotide (e.g., phosphate groups).

For example, FIGS. 1A and 1B illustrate aggregation of particular embodiments of branched compounds having structure (I) with single stranded (ss) nucleic acid (FIG. 1A) and double stranded (ds) nucleic acid (FIG. 1B). Five positive charges (e.g., on nitrogen atoms) of the compounds form five simultaneous ion pairs with five negative charges in the nucleic acid molecules (dotted circles). The spacing among the five positive charges of the compounds having structure (I) with the five negative charges of the nucleic acid molecules is illustrated. In some embodiments, the distance between the positive charges is about 3 to about 10 Å. In some embodiments, the distance between the positive charges is about 4 to about 8 Å. In some embodiments, the distance between the positive charges is about 5 to about 7 Å. For example, the distance between the positive charges is about 6 to about 7 Å and about 5 to about 6 Å in length for four and three carbon atoms chains, respectively.

In some embodiments, the distance between adjacent negative charges in a nucleic acid molecule can be about 3 to about 10 Å. In some embodiments, the distance between adjacent negative charges in a nucleic acid molecule can be about 4 to about 9 Å. In some embodiments, distance between adjacent negative charges in a nucleic acid molecule can be about 5 to about 8 Å. The distance between the negative charges can depend on the steric locations of oxygen atoms of adjacent phosphate groups. Such a configuration brings one or more aziridinyl groups in close proximity to one or more nucleophilic centers of the nucleic acid molecules. Each of the one or more aziridinyl groups can alkylate the nucleic acid molecule. Aziridinyl groups in branched compounds described herein (marked with a star) can reach heterocycles in both a single stranded and a double stranded nucleic acid molecule. The dotted line in FIGS. 1A and 1B illustrate the bonds between the ribose and phosphate groups. In the structures provided in FIGS. 1A and 1B, B represents a nitrogenous (e.g., heterocycle) base, X represents hydrogen (H) or OH, and R corresponds to hydrogen methyl, ethyl, or any monovalent chemical group.

The invention also relates to methods and systems of inactivating one or more nucleic acids in a sample comprising administering a compound to a sample. In some embodiments, the sample comprises one or more nucleic acids to be inactivated. As used herein, "inactivating" or "inactive" means a reaction involving at least one aziridinyl group with a nucleophilic center. The nucleophilic center can be found, for example, in any of the nitrogenous bases shown in FIG. 2. In one embodiment, the method of inactivating one or more nucleic acids in a sample comprises administering a composition comprising a (one or more) compound (e.g., having structure (I) and/or (III)), whereby the compound inactivates each nucleic acid by alkylating the nucleic acid. Alkylation of a nucleic acid can be at any one of the nucleophilic nitrogen atoms in a nitrogenous base (heterocycle) (see FIG. 2).

Figure 2:
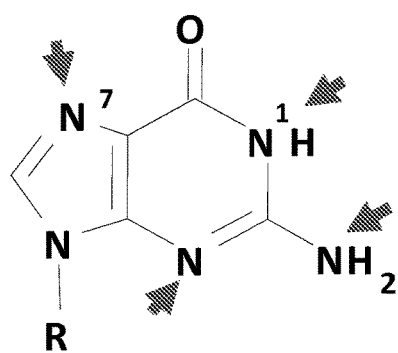
FIG. 2 illustrates nucleophilic sites in DNA and RNA nitrogenous bases.
Figure 2:
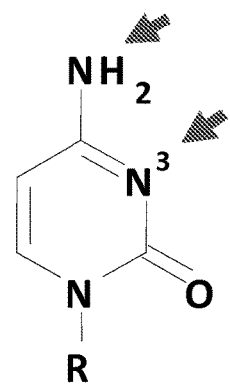
Figure 2:
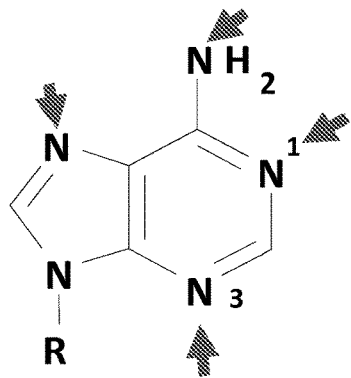
Figure 2:
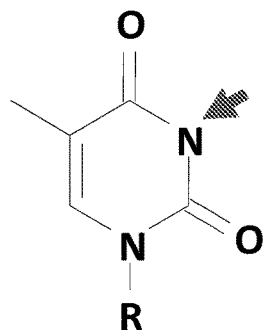
Figure 2:
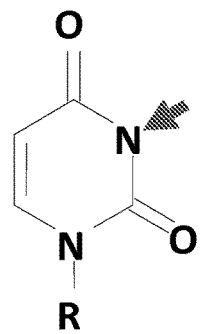

Referring to FIG. 2, nucleophilic centers in the nitrogenous bases of DNA and RNA are shown. For example, N1, N3 and N7 positions in guanine (G) as well as amino group at C2 can be a nucleophilic center. In adenine, nucleophilic centers can be N1, N3 and N7 positions as well as the amino group at C2. In cytosine (C), the amino group at C1 and nitrogen atom at N3 can be nucleophilic. For thymine (T) and uracil (U) the nitrogen atom at position N3 can be nucleophilic. The arrows indicate a location of a nucleophilic nitrogen atom or amino group in the nitrogenous base (e.g., heterocycles) of nucleic acids. Alkylation of a nitrogenous base at any of those locations can prevent replication of DNA, transcription of RNA, and/or translation of proteins that can result in the inactivation of pathogens in a sample.

In some embodiments, the nucleic acid can be from any source, for example, a biological source or sample. In one embodiment, the nucleic acid can comprise nucleic acid from an organism. For example, the organism can be a eukaryote or prokaryote. In another embodiment, the nucleic acid can comprise a bacterial and/or a viral nucleic acid. In another embodiment, the nucleic acid can be natural or synthetic (e.g., man-made). In some embodiments, the nucleic acid in a sample can be single stranded, double stranded, or both. In some embodiments, each of the one or more nucleic acids to be inactivated comprises DNA and/or RNA. In some embodiments, the nucleic acid comprises a pathogen nucleic acid sequence. For example, the pathogen can comprise a blood-borne pathogen. Examples of blood-borne pathogens include, but is not limited to, hepatitis B (HBV), hepatitis C (HCV), human immunodeficiency virus (HIV; Types 1 and 2), malaria, syphilis, brucellosis, babesiosis, leptospirosis, arboviral infections (e.g., Colorado tick fever), relapsing fever, Creutzfeldt-Jakob disease, Chagas disease (Trypanosoma cruzi), West Nile virus (WNV), Human T-lymphotropic virus type I, and viral hemorrhagic fever (e.g., Ebola virus and Marburg virus). In another embodiment, the pathogen nucleic acid sequence is a viral and/or bacterial nucleic acid sequence.

For example, DNA or RNA can be double-stranded helixes and/or single stranded. In some embodiments, the DNA can comprise genomic DNA, dsDNA, ssDNA, cDNA, branched DNA, naturally-occurring DNA, and/or synthetic (e.g., man-made) DNA. In some embodiments, the RNA can comprise mRNA, ncRNA (non-coding RNA), tRNA, miRNA (micro RNA), siRNA (small interfering RNA), ssRNA, dsRNA, antisense RNA, rRNA (ribosomal RNA), tmRNA (transfer-messenger), naturally-occurring RNA and/or synthetic RNA. In some embodiments, the RNA can comprise RNA containing self-complementary sequences that allow their segments to fold and pair with itself to form a double-stranded helix.

As described herein, in some embodiments, the compounds, e.g., compounds having structure (I) or (III), can selectively aggregate with any nucleic acid molecule (e.g., single stranded and/or double stranded DNA and/or RNA). The aggregation of a compound having structure (I) or (III) with a nucleic acid molecule can be due to formation of simultaneous ion-pairing (e.g., formation of one or more ion-pairs between one or more positive charges of compounds having structure (I) or (III) with one or more negative charges of nucleic acid molecules). The inactivation of one or more nucleic acid molecules (e.g., nucleic acid from viruses, prokaryotes and eukaryotes) can occur through alkylation of one or more nucleophilic centers with one or more aziridinyl groups. In some embodiments, the number of aziridinyl groups can be 1, 2, 3, 4, 5, 6, 7, 8, 9, 10, or more having structure (I) and/or (III). In some embodiments, the number of alkylation sites in a nucleic acid molecules can be 1, 2, 3, 4, 5, 6, 7, 8, 9, 10, or more. One of ordinary skill in art can readily appreciate that the number of alkylation sites can be determined by the length of a nucleic acid molecule and/or the number of nucleophilic centers in the nucleic molecule and/or the number of aziridinyl groups in compounds having structure (I) and/or (III).

Figure 3:
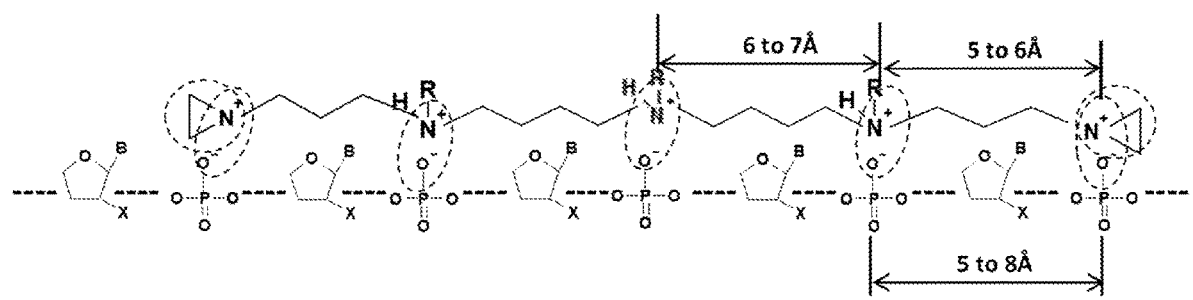
FIG. 3 illustrates aggregation of another embodiment of the compound with a nucleic acid.

Referring to FIG. 3, one embodiment of a compound (e.g., non-branched) described herein having structure (I) illustrates the aggregation with a nucleic acid is illustrated. In this embodiment, five positive charges (e.g., on each nitrogen atom) in the compound can form five ion pairs with five adjacent negative charges in the nucleic acid molecule (dotted circles). The spacing among five positive charges (e.g., on each nitrogen atom) of the compound is about 6 to about 7 Å for 4 carbon chains and about 5 to about 6 Å in length for 3 carbon atoms chains. The distance between adjacent negative charges of a nucleic acid molecule can be about 5 to about 8 Å depending on the location of the oxygen atoms of adjacent phosphate groups. Such aggregations bring one or more aziridinyl groups in close proximity to one or more nucleophilic centers of a nucleic acid molecule. The labels B, X and R are the same as disclosed in FIG. 1 described herein.

In some embodiments, the structures of the compounds (e.g., having structure (I) or (III)) described herein, can possess a branched structure (see, e.g., FIGS. 1A-1B). In other embodiments, the structure of the compounds (e.g., having structure (I) or (III)) described herein, can possess a non-branched (or linear) structure (see, e.g., FIG. 3). In some embodiments, the compounds having structure (I) or (III) described herein have an aziridinyl group at each terminus. In some embodiments, the compounds having structure (I) or (III) have an aziridinyl group at one or more termini.

Figure 4A:
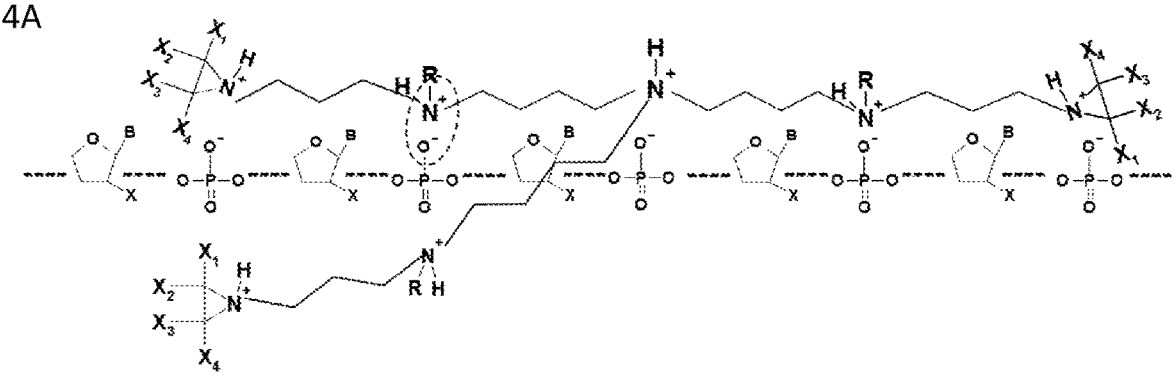
FIGS. 4A-4D illustrates aggregation of other embodiments of the compounds with single stranded nucleic acid molecules.
Figure 4B:
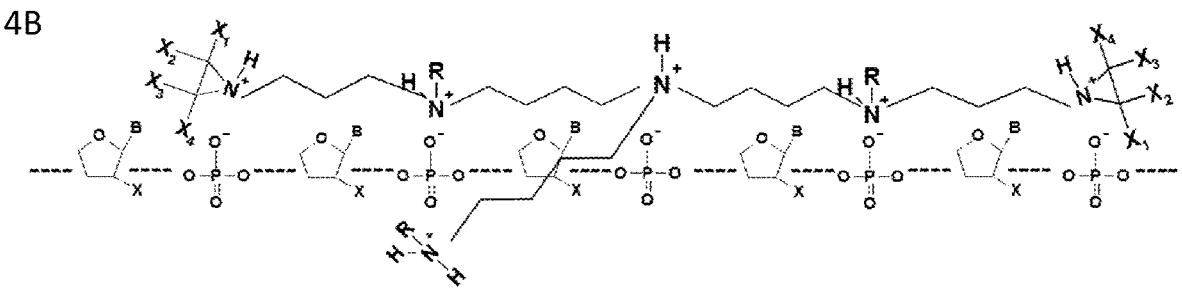
Figure 4C:
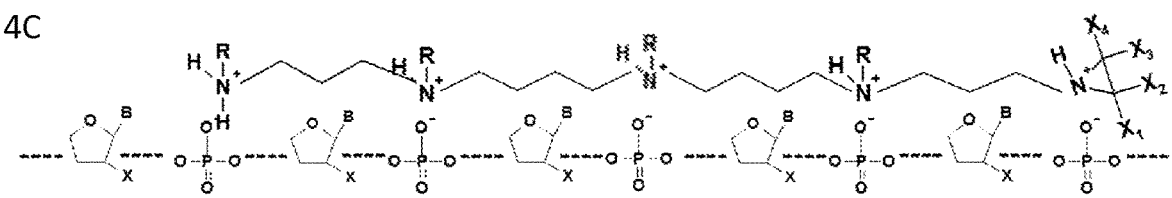
Figure 4D:
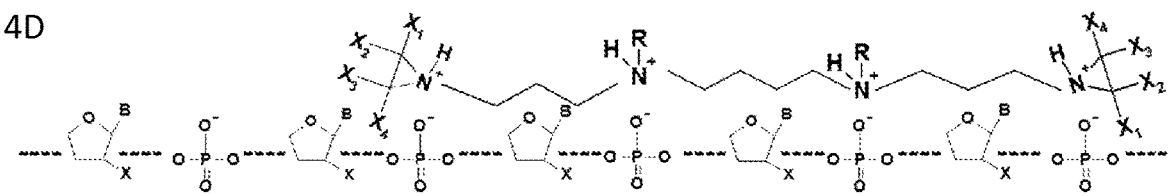

Referring to FIGS. 4A-4D, other embodiments of the compounds are illustrated with single stranded nucleic acid molecules. In FIGS. 4B and 4C, one of the termini of the compounds illustrated is not connected with an aziridinyl group. In FIG. 4A, the compound has 7 total positive charges (e.g., a positive charge on each nitrogen atom), in FIG. 4B, the compound has 6 positive charges, in FIG. 4C, the compound has five positive charges and in FIG. 4D, the compound has four positive charges. In each of FIGS. 4A-4D, the aziridinyl rings atoms can be covalently attached to an atom other than hydrogen. For example, Xi, X2, X3, and X4 can be selected from the group consisting of hydrogen (H), fluorine (F), $CH_3$, $OCH_3$, $CH_2CH_3$, $CH(CH_3)_3$, an alkyl (e.g., straight chained or branched), and any other independently selected monovalent atom or chemical group. B, R, and X are the same as those disclosed in FIGS. 1A-1B.

In some embodiments, the present invention relate to methods of administering compounds and/or compositions comprising compounds for inactivating one or more nucleic acid molecules in a sample. For example, the compounds and compositions described herein can be used to inactivate one or more nucleic acid molecules in a blood sample (e.g., from donated blood). In another embodiment, the method comprises using the compositions and compounds described herein as a chemical inactivator for a vaccine (e.g., dead or inactivated vaccine) production. In yet another embodiment, the method comprises using the compositions and compounds described herein to sterilize one or more products (e.g., medical, pharmaceutical, cosmetic, food, and military products). One of ordinary skill in the art will readily appreciate the compounds described herein can also be used in other methods not described herein.

As previously described, the spacing among the one or more positive charges (e.g., on the nitrogen atoms) of compounds can approximate with the spacing among the one or more negative charges in nucleic acid molecules to form simultaneous ion pairing.

Another feature of the compounds described herein can include the flexibility for one or more aziridinyl groups to react with one or more nucleophilic centers in a nucleic acid molecule. Also, in some embodiments, the reaction can occur at a pH of about 6.0 to about 8.0.

In one embodiment, the compounds described herein can react (e.g. with a nucleic acid molecule) at a temperature of about 1 to about 55° C. In some embodiments, the reaction can occur at about 5 to about 50° C. In some embodiments, the reaction can occur at about 10 to about 45° C. In some embodiments, the reaction can occur at about 25 to about 45° C. In some embodiments, the reaction can occur at about 4° C. In some embodiments, the reaction can occur at about 21° C. In some embodiments, the reaction can occur at about 37° C.

In some embodiments, the compounds are positively charged. In other embodiments, the compounds and compositions are water-soluble. In some embodiments, compounds and compositions can cross a cell membrane, a cell wall, and/or a capsid of an organism. In other embodiments, the compounds and compositions can be used in vitro and/or in vivo.

Figure 5:
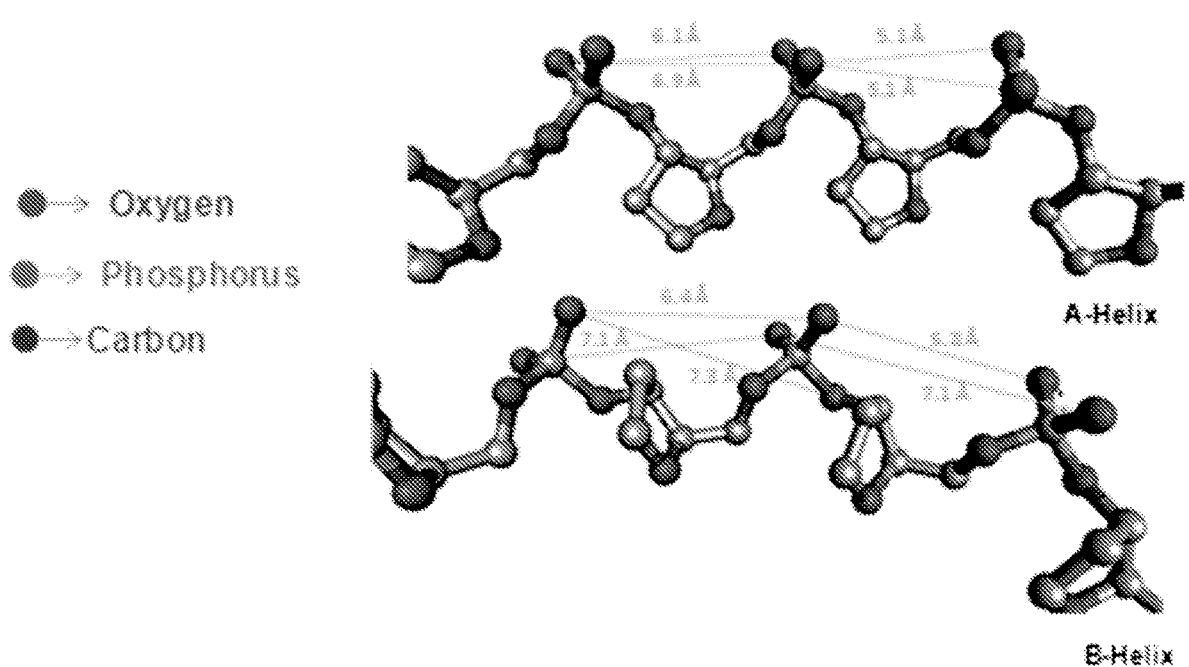
FIG. 5 illustrates variations in length wise spacing of negative charges of two neighboring phosphate groups in the backbones of nucleic acid molecules are.
Figure 7:
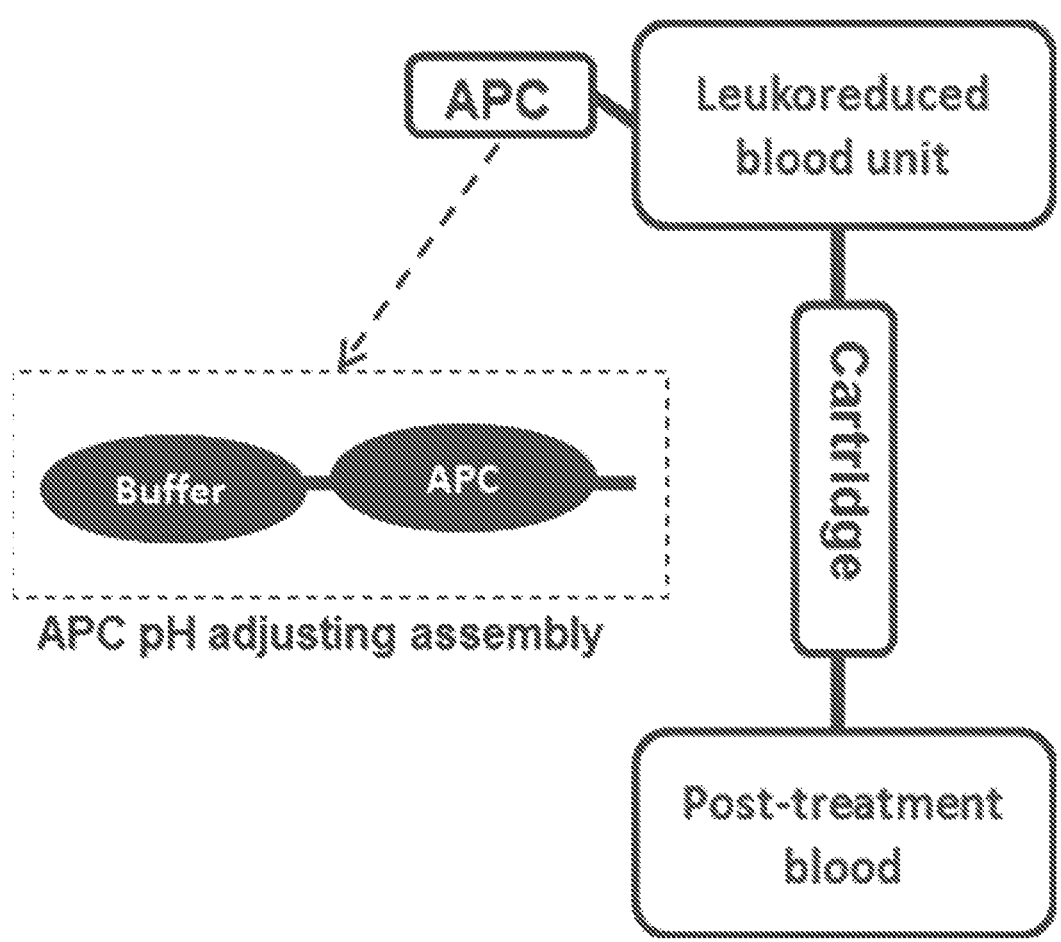
FIG. 7 illustrates a system comprising an anti-pathogen compound (APC) for use in treating a blood or a blood product.
Figure 8:
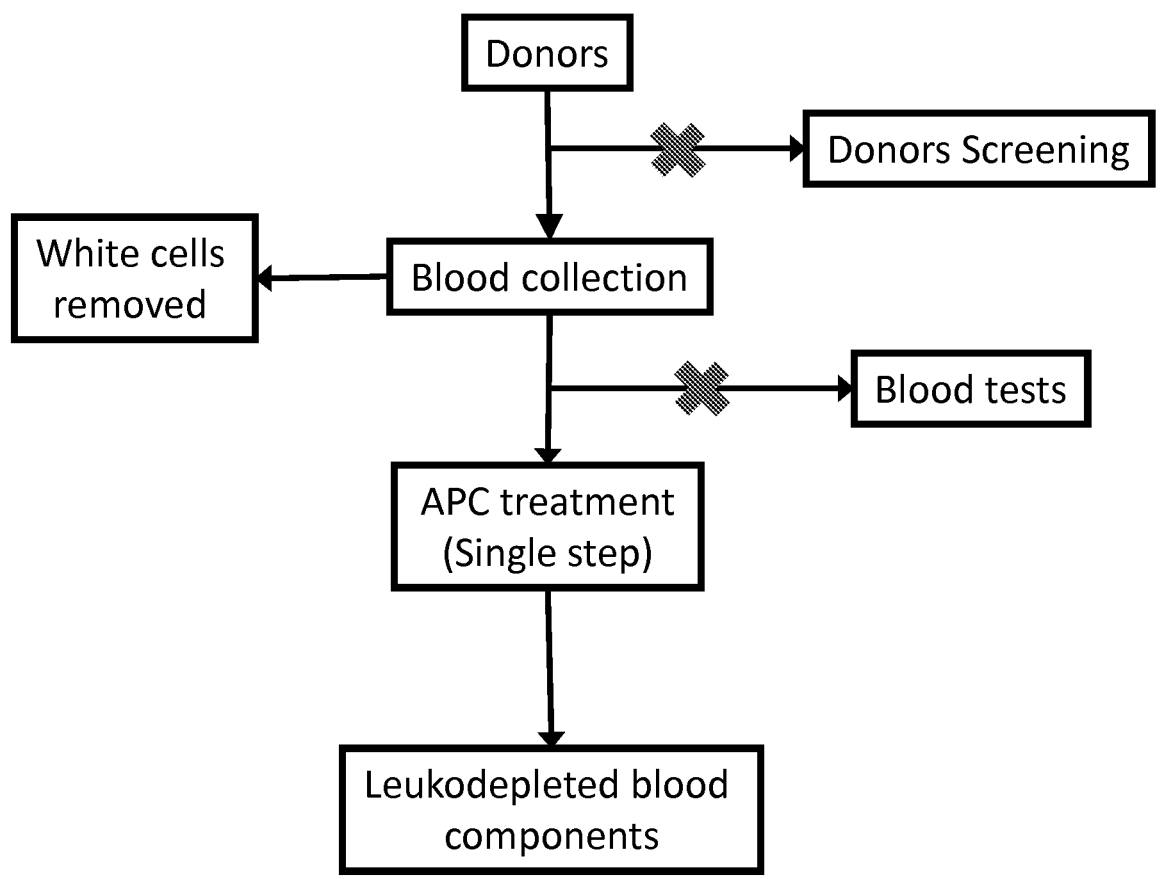
FIG. 8 illustrates a flow diagram for processing a blood or a blood product using the methods described herein.

FIG. 5 illustrates variations in spacing (e.g., length wise) of negative charges of two neighboring phosphate groups in the backbones of a nucleic acid molecule. Depending on the configuration (e.g., A-helix and B-helix), the spacing may vary in range of about 4 to about 9 Å. In FIG. 5, heterocycles (e.g., nitrogenous bases) and hydrogen atoms are not shown. As shown in FIG. 5, a higher probability of distances between the negative charges is in range of about 5 to about 7 Å. In some embodiments, the compounds have one or more positive charges that are separated by a distance of about 5 to about 8 Å. In some embodiments, the compounds have one or more positive charges that are separated by a distance of about 5 to about 7 Å. In some embodiments, the compounds have one or more positive charges are separated by a distance of about the same distance separating the negative charges on a nucleic acid molecule.

Referring to FIGS. 6A-6B, the molecular structures are shown of two embodiments of the compounds described herein, a branched (FIG. 6B) and a linear (FIG. 6A) compound. Various distances between the positive charges are demonstrated. Computer modeling was used with compounds having structure (I). The spacing between positive charges in the compounds shown in FIGS. 6A-6B having structure (I) is about 5.5 to about 6.7 Å, respectively. These distances can coincide with the positions of negative charges shown in FIG. 5.

In some embodiments, the compositions and compounds can be used for the production of blood products, vaccines, sterilized pharmaceutical, cosmetic, medical, and food products, as well as high efficacy therapeutic drugs for the treatment of cancer.

In one embodiment, the method comprises inactivating one or more nucleic acids in a sample. In some embodiments, the sample comprises a biological sample. In some embodiments, the sample comprises a blood and/or a blood product. In some embodiments, a buffy coat has been removed from the blood or blood product. For example, most or all of the white blood cells (wbc) are removed from the blood or blood product prior to inactivating one or more nucleic acids in the sample. In some embodiments, the sample comprises whole blood. In some embodiments, the sample comprises plasma. In some embodiments, the sample comprises platelets. In some embodiments, the sample comprises cryoprecipitate. In some embodiments, the sample is a blood substitute (e.g., artificially produced product).

In some embodiments, the sample comprises a cosmetic composition. In another embodiment, the sample comprises a medical composition. In another embodiment, the sample is used for a vaccine or vaccine production.

The compositions and compounds can be synthesized by the methods disclosed herein. One of ordinary skill in the art can readily appreciate different chemical approaches and synthetic schemes. The following examples, such as the synthesis of the compositions and compounds, are provided for illustrative purposes only and are in no way intended to limit the scope of the present invention.

EXEMPLIFICATION

Example 1

Synthesis of Tri-(N-(3-(aziridin-1-yl)propyl)-N-methyl-4-aminobutyl)amine (Compound V)

8 g (200 mmol) aziridine (MW=43) (I) is dissolved in 80 mL of diethyl ether and added drop wise to a solution of 11.2 g (200 mmol) of acrolein (compound II) (MW=56) dissolved in 80 ml of diethyl ether on an ice bath placed on magnetic mixer plate. After the completion of adding, reaction mixture is stirred (for another hour on ice bath (4° C.) and concentrated on a rotary evaporator to remove diethyl ether from 3-aziridinylpropanal (MW=99) (compound III). 17 g (~150 mmol) of crude 3-aziridinylpropanal (compound III) is dissolved in 140 ml of methanol and added drop wise to a solution of 13.7 g (50 mmol) tri(4-(methylamino)butyl)amine (compound IV) dissolved in 140 mL of methanol. After stirring reaction mixture (RM) for 20 minutes at room temperature (RT), 8 g of $NaBH_4$ reducing agent is added in 0.5 g portions at 5-6 minute intervals. After stirring overnight (or 12 hrs), excess $NaBH_4$ is neutralized by slowly adding 10.0 N methanolic-HCl. The reaction mixture is evaporated containing the final product, Tri-(N-(3-(aziridin-1-yl)propyl)-N-methyl-4-aminobutyl)amine (compound V), on a rotary evaporator to near dryness. Remaining residue is dissolved in 120-140 ml of water and adjusted to pH 12 with 40% (w/w) NaOH. Resulting solution is extracted with 120 ml of diethyl ether three times. All three diethyl ether extract fractions are combined and dried over $Na_2SO_4$. The final product is purified by chromatography or fractional distillation under vacuum. The synthesis of Tri-(N-(3-(aziridin-1yl)propyl)-N-methyl-4-aminobutyl)amine ($C_{30}H_{63}N_7$, MW=521) (compound V) is shown below.

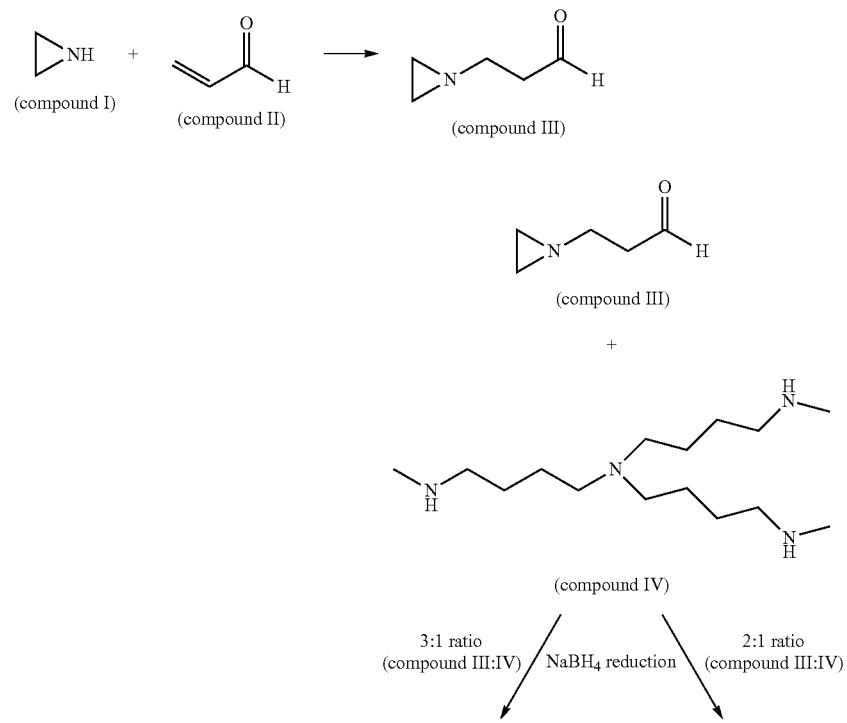

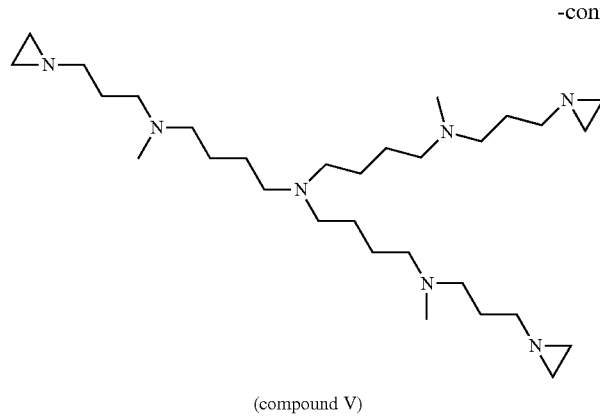

(compound V)

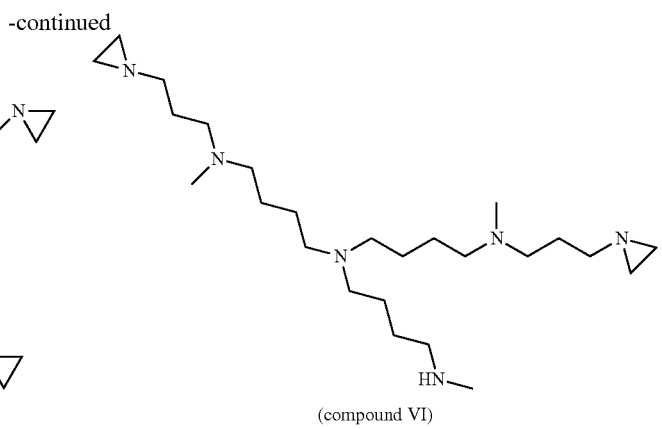

(compound VI)

Example 2

Di-(N-(3-(aziridin-1yl)propyl)-N-methyl-4-aminobutyl) (N-methyl-4-aminobutyl)amine (Compound VI)

3-aziridinylpropanal (compound III) is synthesized as described in Example 1 above. 10 g (~100 mmol) of 3-aziridinylpropanal (compound III) is dissolved in 100 mL of methanol and added drop wise to a solution of 13.7 g (50 mmol) tri(4-(methylamino)butyl) amine (compound IV) dissolved in 140 ml of methanol. After stirring for 20 minutes at room temperature, 8 g of $NaBH_4$ reducing agent is added in 0.5 g portions in 5-6 minute intervals. After stirring overnight (or 12 hrs), excess of $NaBH_4$ is neutralized by slowly adding 10.0 N methanolic-HCl. The reaction mixture containing the final product, Di-(N-(3-(aziridin-1yl)propyl)-N-methyl-4-aminobutyl) (N-methyl-4-aminobutyl)amine (VI) is evaporated on a rotary evaporator to near dryness. The remaining residue is dissolved in 120-140 ml of water and adjusted to pH 12 with 40% (w/w) NaOH. The resulting solution is extracted with 120 ml of diethyl ether three times. All three diethyl ether extract fractions are combined and dried over $Na_2SO_4$. Final product is purified by chromatography or fractional distillation under vacuum. The synthesis of Di-(N-(3-(aziridin-lyl)propyl)-N-methyl-4-aminobutyl) (N-methyl-4-aminobutyl)amine (compound VI) ($C_{25}H_{53}N_6$, MW=437) is shown above.

Example 3

Synthesis of 1,17-Di(aziridin-1-yl)-4,14-dimethy-9-ethyl-4,9,14-triazaheptadecane (Compound VIII)

3-aziridinylpropanal (compound III) is synthesized as described in Example 1. ~100 mmol of 3-aziridinylpropanal (compound III) is dissolved in 100 ml of methanol and added drop wise to a solution of 50 mM 7-ethyl-2,7,12-triazatridecane (compound VII) dissolved in 140 ml of methanol. After stirring for 20 minutes at room temperature, 8 g of $NaBH_4$ reducing agent is added in 0.5 g portions at 5-6 minute intervals. After stirring overnight (or 12 hrs), excess of $NaBH_4$ is neutralized by slowly adding 10.0 N methanolic-HCl. The reaction mixture containing the final product, 1,17-di(aziridin-1-yl)-4,14-dimethy-9-ethyl-4,9,14-triazaheptadecane (compound VIII) is evaporated on a rotary evaporator to near dryness. Remaining residue is dissolved in 120-140 ml of water and adjusted to pH 12 with 40% (w/w) NaOH. The resulting solution is extracted with 120 ml of diethyl ether three times. All three diethyl ether extract fractions are combined and dried over $Na_2SO_4$. The final product is purified by chromatography or fractional distillation under vacuum. The structure of compounds (compound VII) 7-ethyl-2,7,12-triazatridecane compound and (compound VIII) 1,17-di(aziridin-1-yl)-4,14-dimethy-9-ethyl-4,9,14-triazaheptadecane ($C_{22}H_{47}N_5$, MW=381.65) are shown below.

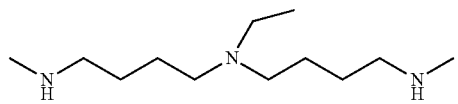

(Compound VII)

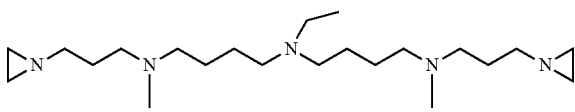

(Compound VIII)

Example 4

Synthesis of 8-(N-(3-(aziridin-1-yl)propyl)-2-aminoethyl)-1,16-di(aziridin-1-yl)-4,8,13-triazahexadecane (Compound X)

3-aziridinylpropanal (compound III) is synthesized as in described in Example 1. 17 g (~150 mmol) of 3-aziridinylpropanal (compound III) is dissolved in 140 mL of methanol and added drop wise to a solution of 50 mmol 4-(2-aminoethy)-4-azaoctane-1,8-diamine (compound IX) dissolved in 140 mL of methanol. After stirring for 20 minutes at room temperature, 8 g of $NaBH_4$ reducing agent is added in 0.5 g portions at 5-6 minute intervals. After stirring overnight (or 12 hrs), excess of $NaBH_4$ is neutralized by slowly adding 10.0 N methanolic-HCl. The reaction mixture containing the final product, 8-(N-(3-(aziridin-1-yl)propyl)-2-aminoethyl)-1,16-di(aziridin-1-yl)-4,8,13-triazahexadecane (X), is evaporated on a rotary evaporator to near dryness. The remaining residue is dissolved in 120-140 ml of water and adjusted to pH 12 with 40% (w/w) NaOH. The resulting solution is extracted with 120 ml of diethyl ether three times. All three diethyl ether extract fractions are combined and dried over $Na_2SO_4$. The final product is purified by chromatography or fractional distillation under vacuum or separated on an ion-exchange column. The structure of compounds (compound IX) 4-(2-aminoethy)-4-azaoctane-1,8-diamine and (compound X) 8-(N-(3-(aziridin-1-yl)propyl)-2-aminoethyl)-1,16-di(aziridin-1-yl)-4,8,13-triazahexadecane ($C_{24}H_{51}N_7$, MW=437) are shown below.

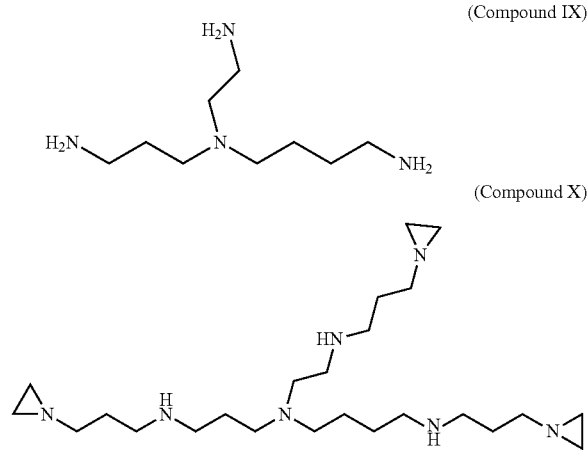

(Compound IX)

(Compound X)

Example 5

Synthesis of 1,12-Di(aziridin-1-yl)-4,9-dimethyl-4,9-diazadodecane (Compound XII)

3-aziridinylpropanal (compound III) is synthesized as described in Example 1 above. ~100 mmol of 3-aziridinylpropanal (compound III) is dissolved in 100 ml of methanol and added drop wise to a solution of 50 mmol N,N'-Dimethyl-1,4-butanediamine (compound XI) dissolved in 140 ml of methanol. After stirring for 20 minutes at room temperature, 8 g of NaBH$_4$ reducing agent is added in 0.5 g portions at 5-6 minute intervals. After stirring overnight (or 12 hrs), excess of NaBH$_4$ is neutralized by slowly adding 10.0 N methanolic-HCl. The reaction mixture containing the final product, 1,12-Di(aziridin-1-yl)-4,9-dimethyl-4,9-diazadodecane (compound XII) is evaporated on a rotary evaporator to near dryness. The remaining residue is dissolved in 120-140 ml of water and is adjusted to a pH 12 with 40% (w/w) NaOH. The resulting solution is extracted with 120 ml of diethyl ether three times. All three diethyl ether extract fractions are combined and dried over Na$_2$SO$_4$. The final product is purified by chromatography or fractional distillation under vacuum. The structure of compounds (compound XI) N,N'-Dimethyl-1,4-butanediamine compound and (compound XII) 1,12-Di(aziridin-1-yl)-4,9-dimethyl-4,9-diazadodecane ($C_{16}H_{34}N_4$, MW=282) are shown below.

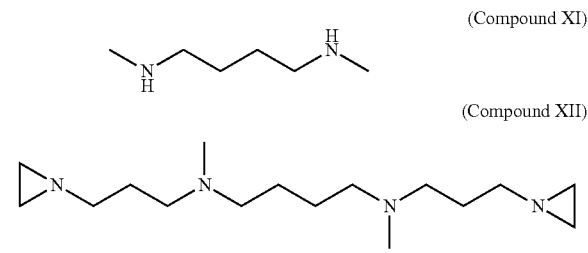

(Compound XI)

(Compound XII)

Example 6

Synthesis of 1,13-di(aziridin-1-yl)-4,10-diaza-7-oxatridecane (Compound XIV)

3-aziridinylpropanal (compound III) is synthesized as described in Example 1, above. 10 g (~100 mmol) of 3-aziridinylpropanal (compound III) (MW=99) is dissolved in 140 ml of methanol and added drop wise to a solution of 11.5 g (50 mmol) of di-(2-aminoethyl)ether (compound XIII) dissolved in 140 mL of methanol. After stirring the reaction mixture for 20 minutes at room temperature, 8 g of NaBH$_4$ reducing agent is added in 0.5 g portions at 5-6 min intervals. After stirring overnight (or 12 hrs), an excess of NaBH$_4$ is neutralized by slowly adding 10.0 N methanolic-HCl. The reaction mixture containing the final product, 1,13-di(aziridin-1-yl)-4,10-diaza-7-oxatridecane (compound XIV) is evaporated on a rotary evaporator to near dryness. The remaining residue is dissolved in 120-140 ml of water and adjusted to pH 12 with 40% (w/w) NaOH. The resulting solution is extracted with 120 ml of diethyl ether three times. All three diethyl ether extract fractions are combined and dried over Na$_2$SO$_4$. The final product is purified by chromatography or fractional distillation under vacuum. The synthesis of 1,13-di(aziridin-1-yl)-4,10-diaza-7-oxatridecane (compound XIV) ($C_4H_{30}N_4O$, MW=270) is shown below.

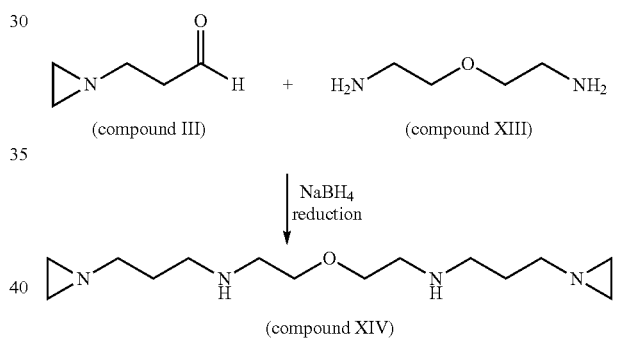

(compound III)    (compound XIII)

NaBH$_4$ reduction (compound XIV)

Example 7

In some embodiments, the compounds described herein, or anti-pathogen compounds (APC), can be used in closed delivery systems for the inactivation of one or more nucleic acids in a donated blood sample. A closed system enabling the APC delivery and its removal from post-treatment blood has been developed and a schematic of such a system is shown in FIG. 6.

A buffer is infused in an APC containing pouch followed by infusion of a pH adjusted APC into leukodepleted blood (e.g., white blood cells are removed) unit and incubated. Residual APC and products of its degradation are removed by a free flow though disposable cartridge integrated into closed blood sterilization assembly.

A pH-adjusted APC can be infused or previously added in a leukodepleted blood unit at a final therapeutic concentration and incubated at about room temperature (e.g., 21° C.). After completion of the treatment, any residual APC and products of its degradation can be removed by free flow filtration (e.g., on a cation exchange disposable cartridge). A cartridge (e.g., spiral-shaped, smooth surface and large diameter) comprising negatively charged beads can enable a controllable retention time using free flow filtration. Some APCs can be inside red blood cells and controlling the retention time can enable the full diffusion of APCs from red blood cells and be filtered by the negatively charged disposable cartridge.

Example 8

Quenching of Residual Compositions of Matter

Chemical quenching of residual compositions and compounds having structure (I) in a post-treatment sample is possible when needed. Some or all (e.g, about 50% or more, about 75% or more, about 80% or more, about 90% or more, about 95% or more, or about 99% or more) of the compounds can be quenched by using different nucleophilic small molecules. For example, such molecules can be molecules that enable conversion of aziridinyl groups into a neutral and/or nontoxic compounds, such as, thiophosphates or thiosulphates. Quenching can take place in a sample by direct infusion of the quencher compound dissolved in water or water based solvents. Examples of quencher compounds include, but is not limited to, cysteine, hydrogen sulfate, methylmercaptan, adenosine, guanosine, or any small molecule comprising a nucleophilic center.

The chemical quenching of aziridinyl rings is shown below.

Example 9

Production of an Inactivated Vaccine

For the production of an inactivated vaccine (i.e. killed pathogen), a virus particle or other pathogen is grown in culture and can be killed with one or more of the compounds disclosed herein with adopting of methods used for killing of pathogens by formaldehyde. (Thierry-Carstensen et al (2013) Vaccine. 2013 31(45):5178-91; Verma et al (2013) Hum Vaccin Immunother. 9(4):763-5; Aoki et al (2010) Crit Rev Immunol. (2):167-87; Bovier P A. (2008) Expert Rev Vaccines. 7(8):1141-50; Griffin et al (2008) Front Biosci. 13:1352-70). Specific features of the compounds disclosed herein can allow the full inactivation of the nucleic acid from the pathogen (e.g., virus). Vaccine efficacy can be maximized by using of low concentration of the compounds having structure (I) then compared to the amount of formaldehyde currently used.

A microorganism (e.g., bacteria, virus, protozoa) is grown in vitro and/or in vivo. A compound having structure (I) and/or (III) is added into a system containing the microorganism. The compound can penetrate through cell membranes, cell walls, and capsids. The compound can aggregate and inactivate nucleic acid present in the microorganism, as illustrated in FIGS. 1 to 4. Any residual compound (I) can be removed, for example, using the methods disclosed in example 8.

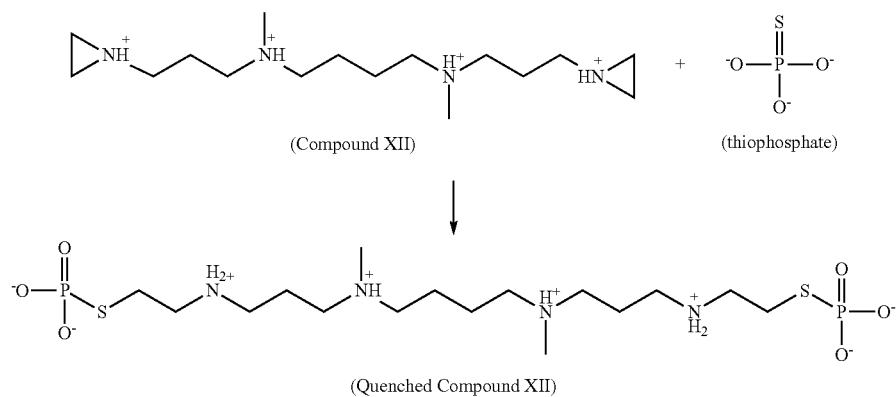

Aziridinyl groups can be neutralized (e.g., reduced) by hydrolysis:

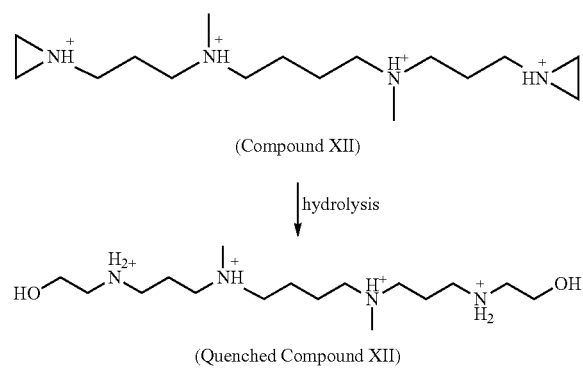

Example 10

Inactivation of Pathogens in Medical and Cosmetic Compositions

The compounds (APCs) described herein can be directly added to a other (e.g., medical and/or a cosmetic) compositions to inactivate one or more nucleic acid molecules. The compounds can be added at a specified concentration and incubated for the certain duration of time defined for the each particular composition separately. Certain compositions, for example, water-based compositions, can be sold after degradation of the APCs. Residual APCs can be quenched to a safe concentration as disclosed in Example 8.

Example 11

Inactivation of a Pathogen on Surfaces

One or more APCs (e.g., compounds having structure (I) and/or (III)) at certain concentrations can be used as the active ingredient in the sterilization of surfaces, for example, in the medical, pharmaceutical, device, and/or food industry. APCs can be in the form of a spray or wipe for the sterilization of surfaces. Direct contact of an APC to a pathogen deposited on the surface can inactivate and/or kill them. Any remaining APC can be wiped from surface with sterile tissue or cloth, washed with sterile solvents, hydrolyzed, or quenched with other sterile compositions if needed.

Those having ordinary skill in the art will appreciate that various changes can be made to the above exemplary embodiments without departing from the scope of the invention.

The invention claimed is:

1. A compound having the structure:

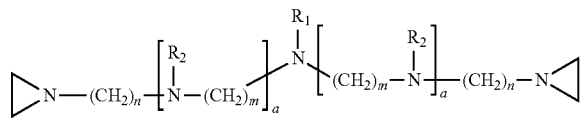

wherein
R$^1$ is selected from the group consisting of CH$_3$, CH$_2$CH$_3$, CH(CH$_3$)$_2$;
R$^2$ is CH$_3$;
a is, independently for each occurrence, 0, 1, 2 or 3, wherein each occurrence of a is not simultaneously selected to be 0;
m is, independently for each occurrence, 2, 3, 4 or 5; and
n is, independently for each occurrence, 2, 3, 4 or 5;
or a pharmaceutically acceptable salt, hydrate, or solvate thereof.

2. The compound of claim 1, wherein each m is, independently for each occurrence, 3 or 4.

3. The compound of claim 2, wherein each n is, independently for each occurrence, 2, 3 or 4.

4. The compound of claim 2, wherein each n is 3.

5. The compound of claim 4, wherein R$^1$ is CH$_3$.

6. The compound of claim 1, wherein R$^1$ is CH$_3$, a first a is 0 and a second a is 1; m is 4; and each n is 3.

7. The compound of claim 2, wherein R$^1$ is CH$_3$, each a is 1 and each n is 3.

8. A method of inactivating one or more pathogen nucleic acids in a sample comprising:
contacting the sample with a compound having structure:

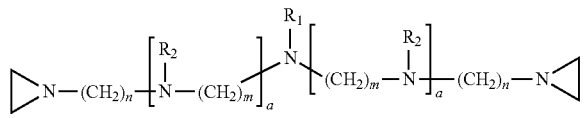

wherein
R$^1$ is selected from the group consisting of CH$_3$, CH$_2$CH$_3$, CH(CH$_3$)$_2$;
R$^2$ is CH$_3$;
a is, independently for each occurrence, 0, 1, 2 or 3, and wherein each occurrence of a is not simultaneously selected to be 0;
m is, independently for each occurrence, 2, 3, 4 or 5; and
n is, independently for each occurrence, 2, 3, 4 or 5;
or a pharmaceutically acceptable salt, hydrate, or solvate thereof; and
wherein the sample comprises one or more pathogen nucleic acids to be inactivated.

9. The method of claim 8, wherein the one or more pathogen nucleic acids is a viral and/or bacterial and/or protozoan nucleic acid.

10. The method of claim 8, wherein the sample comprises a blood, a blood product, or a combination thereof.

11. The method of claim 8, wherein each m is, independently for each occurrence, 3 or 4.

12. The method of claim 11, wherein each n is, independently for each occurrence, 2, 3 or 4.

13. The method of claim 11, wherein each n is 3.

14. The method of claim 13, wherein R$^1$ is CH$_3$.

15. The method of claim 8, wherein R$^1$ is CH$_3$, a first a is 0 and a second a is 1; m is 4; and each n is 3.

16. The method of claim 11, wherein R$^1$ is CH$_3$, each a is 1 and each n is 3.

17. The method of claim 8, wherein the sample is used in the production of a vaccine.

18. A method of producing a vaccine to a pathogen comprising:
contacting a sample comprising the pathogen with a compound having the structure:

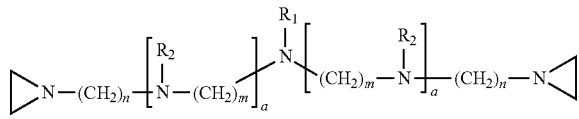

wherein
R$^1$ is selected from the group consisting of CH$_3$, CH$_2$CH$_3$, CH(CH$_3$)$_2$;
R$^2$ is CH$_3$;
a is, independently for each occurrence, 0, 1, 2 or 3, and wherein each occurrence of a is not simultaneously selected to be 0;
m is, independently for each occurrence, 2, 3, 4 or 5; and
n is, independently for each occurrence, 2, 3, 4 or 5;
or a pharmaceutically acceptable salt, hydrate, or solvate thereof.

19. The method of claim 18, wherein the pathogen is a virus.

20. The method of claim 18, wherein the pathogen is a bacterium.

21. The method of claim 18, wherein the pathogen is a protozoa.

22. The method of claim 18, wherein each m is, independently for each occurrence, 3 or 4.

23. The method of claim 22, wherein each n is, independently for each occurrence, 2, 3 or 4.

24. The method of claim 22, wherein each n is 3.

25. The method of claim 24, wherein R$^1$ is CH$_3$.

26. The method of claim 18, wherein R$^1$ is CH$_3$, a first a is 0 and a second a is 1; m is 4; and each n is 3.

27. The method of claim 22, wherein R$^1$ is CH$_3$, each a is 1 and each n is 3.

* * * * *